United States Patent [19]
Stormbom

[11] Patent Number: 5,625,139
[45] Date of Patent: Apr. 29, 1997

[54] METHOD OF MEASURING CONCENTRATION OF NONPOLAR GASES SUCH AS CARBON DIOXIDE BY MEANS OF A POLYMER-BASED SENSOR AND CONCENTRATION SENSOR STRUCTURE

[75] Inventor: Lars Stormbom, Vantaa, Finland

[73] Assignee: Vaisala Oy, Helsinki, Finland

[21] Appl. No.: 544,736

[22] Filed: Oct. 18, 1995

[30] Foreign Application Priority Data

Oct. 21, 1994 [FI] Finland ................................ 944950

[51] Int. Cl.$^6$ .................................................. G01N 7/00
[52] U.S. Cl. ................................ 73/23.21; 73/31.02
[58] Field of Search ...................... 73/29.05, 31.01, 73/31.02, 31.05, 23.21, 23.31, 24.01, 24.04, 24.06

[56] References Cited

U.S. PATENT DOCUMENTS 4,730,479  3/1988  Pyke et al. .

*Primary Examiner*—Hezron E. Williams
*Assistant Examiner*—Jay L. Politzer
*Attorney, Agent, or Firm*—Birch, Stewart, Kolasch & Birch, LLP

[57] ABSTRACT

The invention relates to a method and sensor structure for measuring the concentration of nonpolar gases such as carbon dioxide. According to the method, the concentration of the nonpolar gas adsorbed/absorbed in a polymer film (2) is determined by detecting the weight of the polymer film (2). According to the invention, the dielectric coefficient of the polymer film (2) is measured, and on the basis of this, a correction is made in the concentration measurement result obtained from the weight measurement. (FIG. 1)

8 Claims, 2 Drawing Sheets

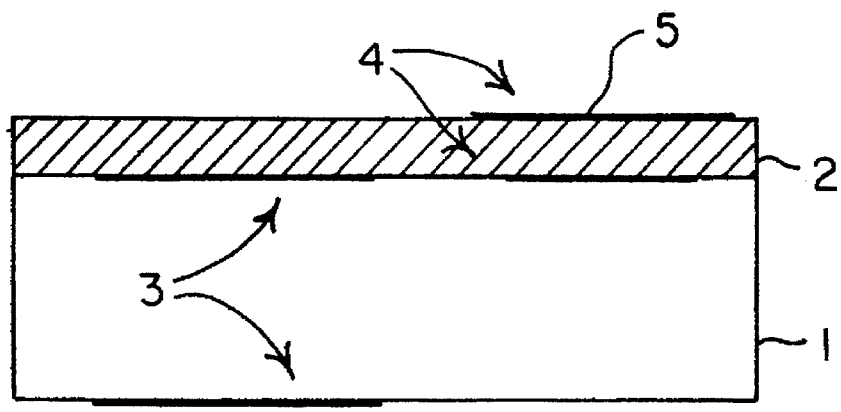
FIG. IA
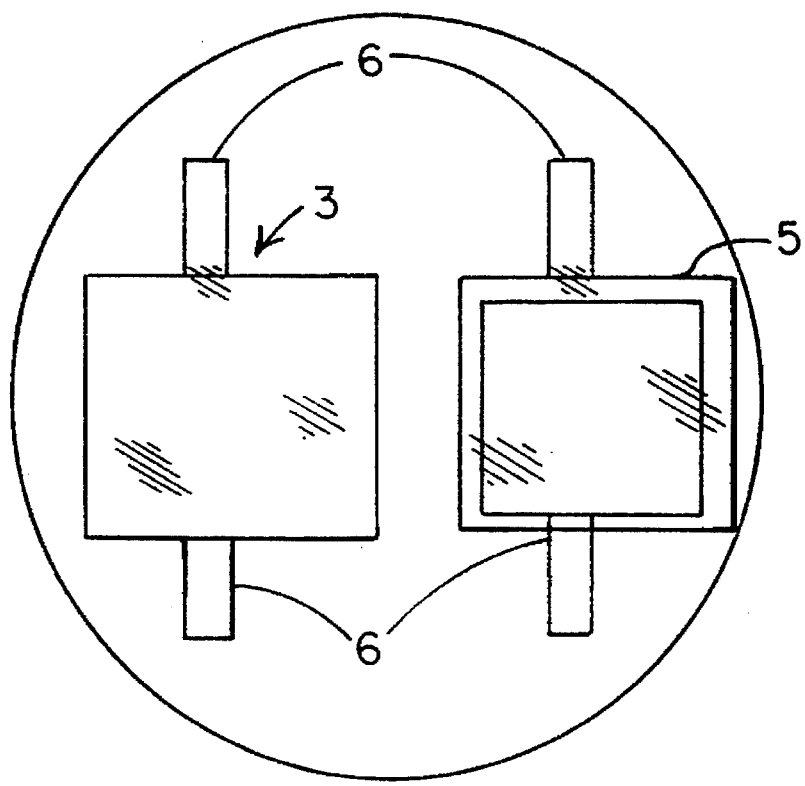
FIG. IB

METHOD OF MEASURING CONCENTRATION OF NONPOLAR GASES SUCH AS CARBON DIOXIDE BY MEANS OF A POLYMER-BASED SENSOR AND CONCENTRATION SENSOR STRUCTURE

The invention is related to a method according to the preamble of claim 1 for measuring the concentration of nonpolar gases such as carbon dioxide by a means of a polymer-based sensor.

The invention also concerns a concentration sensor structure.

Water is generally absorbed in significant amounts in all polymers. When besides water, concentrations of other gases are also desired to be measured using methods based on weighing a polymer film utilizing, e.g., a film-coated quartz crystal or a surface acoustic wave component, the presence of water forms a strongly disturbing factor. With variations in the relative humidity of air, the amount of absorbed/adsorbed water, and resuitingly, the weight of the polymer film, changes.

It is an object of the present invention to overcome the drawbacks of the above-described techniques and to achieve an entirely novel type of method and sensor structure for measuring the concentration of nonpolar gases such as carbon dioxide by means of a polymer-based sensor.

The goal of the invention is achieved by detecting the amount of humidity (that is, water) absorbed/adsorbed in a polymer film through measuring the dielectric coefficient $\epsilon$ of the film, in practice, through measuring the capacitance of the sensor structure. Thus, the effect of humidity can be eliminated in the measurement of another nonpolar gas (such as $CO_2$) based on the weighing of the polymer film.

More specifically, the method according to the invention is characterized by what is stated in the characterizing part of claim 1.

Furthermore, the sensor structure according to the invention is characterized by what is stated in the characterizing part of claim 4.

The invention offers significant benefits.

As the effect of relative humidity variations can be eliminated almost completely, the accuracy of the concentration measurement of a nonpolar gas can be essentially increased.

In the following, the invention will be examined in more detail by means of exemplifying embodiments with reference to the attached drawings, in which:

FIG. 1A is a longitudinally sectional side view of a sensor structure according to the invention;

FIG. 1B is a top view of the sensor structure illustrated in FIG. 1A with the upper electrode, the polymer film and the crystal shown transparent;

Figure 2:
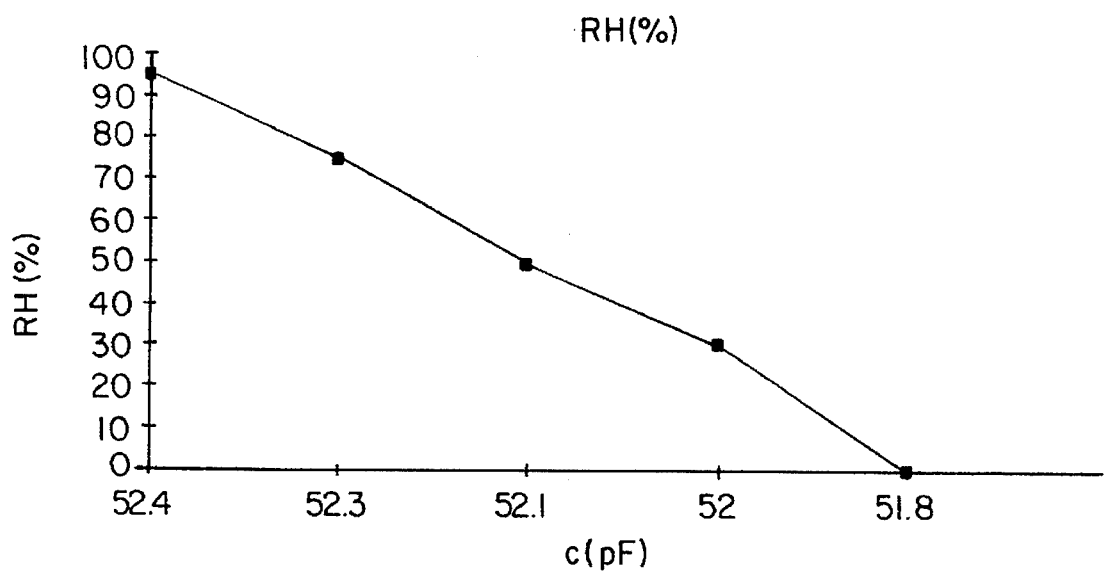
FIG. 2 is a graph showing the effect of relative humidity on the sensor capacitance.

Next, an example is given of the measurement algorithm according to the invention.

A response function of the film mass is defined for the gas to be measured:

$$p_k = f_1(S_1),$$

where $p_k$ = partial pressure of the gas to be measured, and
$S_1$ = film-mass-related output variable of the sensor (e.g., oscillating frequency).

Typically, the function $f_1$ may be a polynomial:

$$p_k = \sum_{i=0}^{n} a_i \cdot S_1^i,$$

where $a_i$ is a constant.

The relationship of the polymer film capacitance with the mass of the polymer film is determined over the entire range of relative humidity at zero concentration of the gas to be measured:

$$S_{1rh} = f_2(C),$$

where

C is the capacitance of the sensor structure,

Typically, the function $f_2$ may be a polynomial:

$$S_{1rh} = \sum_{i=0}^{m} b_i \cdot C^i,$$

where $b_i$ is a constant.

At low concentrations of the gas to be measured, as is typical in environmental measurements, the amount of adsorbed/absorbed water has an insignificant effect on the sorption of the gas to be measured. Then, the partial pressure of the gas to be measured can be computed when the total mass $S_{tot}$ and the capacitance C of the polymer film are known:

$$p_k = f_1(S_{tot} - f_2(C))$$

At high partial pressures of the gas to be measured, the amount of adsorbed/absorbed water affects the sorption of the gas to be measured. Then, the foregoing method must be generalized:

$$p_k = f_3(S_{tot}, C)$$

An exemplary form of function $f_3$ could be written as:

$$p_k = \sum_{i=0}^{n} \left[ \sum_{j=0}^{m} a_{ij} \cdot S_{tot}^i \cdot C^j \right],$$

In the following a practical example is described with reference to the sensor structure illustrated in FIGS. 1A and 1B. Referring to FIG. 1, a quartz crystal 1 is coated with a polymer film 2. Prior to coating, the resonant frequency of the crystal 1 was approx. 11 MHz. After coating the crystal 1 with the film 2, the resonant frequency dropped by about 60 kHz. The thickness of the film 2 may be varied in the range 0.1–10 μm, and typically, the thickness of the film is approx. 1 μm. On top of the crystal 1 are formed a first electrode structure 3 for generating the oscillations and a second electrode structure 4 for measuring the capacitance. The upper surface electrode 5 of the second electrode structure 4 formed on the polymer film 2 is made permeable to the gas to be measured. The electrodes are connected at the contact areas 6 to measurement and control circuits (not shown).

The capacitance of the second electrode structure 4 in the sensor was measured at 100 kHz measurement frequency, and the resonant frequency change of the crystal 1 as a function of relative humidity is given in the following table:

| RH [%] | C [pF] | df [kHz] |
|---|---|---|
| 0 | 51.76 | 0.0 |
| 30 | 51.97 | −22.7 |
| 50 | 52.11 | −38.5 |
| 75 | 52.28 | −58.8 |
| 95 | 52.42 | −75.0 |

In can be seen from the table that the change of resonant frequency is linearly proportional to sensor capacitance with a slope df/dC=−144.4. The graph corresponding to the table is plotted in FIG. 2.

The next table gives the measurement results as a function of ambient relative humidity at two different concentrations of $CO_2$.

| RH [%] | C [pF] | df [at 0 ppm] | df [at 500 ppm] | df [at 1000 ppm] |
|---|---|---|---|---|
| 0 | 51.76 | 0.0 | −29.5 | −57.5 |
| 30 | 51.97 | −22.7 | −51.5 | −80.4 |
| 50 | 52.11 | −38.5 | −66.7 | −95.2 |
| 75 | 52.28 | −58.8 | −85.5 | −114.5 |
| 95 | 52.42 | −75.0 | −101.3 | −129.1 |

Figure 3:
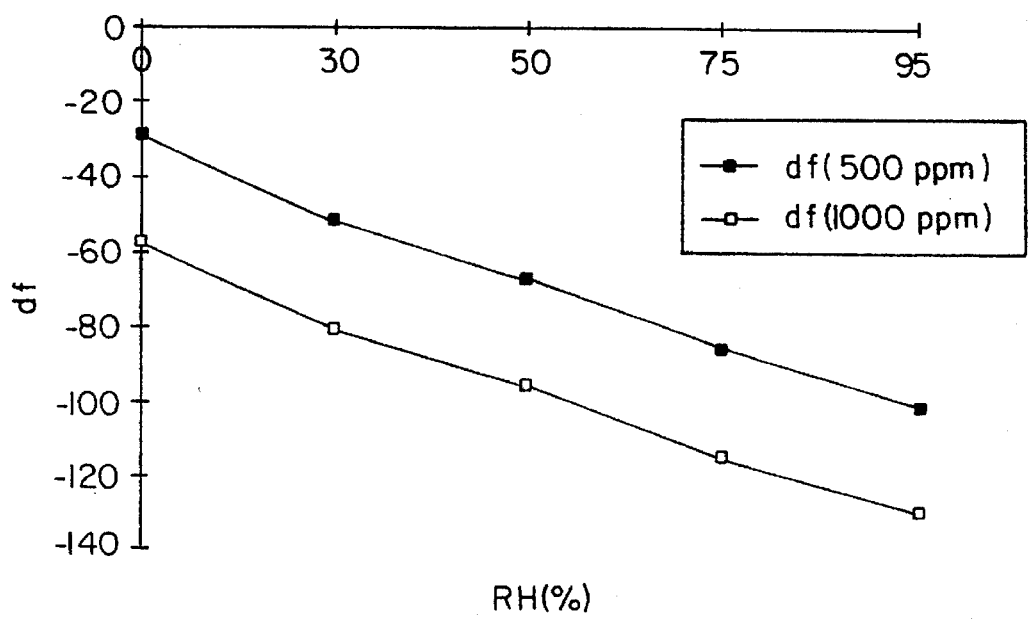
FIG. 3 is a graph showing the change of the crystal oscillating frequency as a function of relative humidity at two different $CO_2$ concentrations.

Now it can be seen from the table that the capacitance of the sensor structure stays unchanged. Not even a 1000 ppm concentration of $CO_2$ could be detected unless the sensor capacitance is known. The graphs corresponding to the results given in the table are plotted in FIG. 3.

The algorithm described above is now applied in the simplest possible form:

Frequency change df is chosen as the measurement variable indicating the weight of the polymer film. By fitting a line between the measurement results of 0 ppm and 1000 ppm at 0 % RH, we obtain:

$$PPM_{CO2} = -17.4 \cdot df$$

The simplest formula describing the effect of humidity as a change of crystal resonant frequency is $df_{rh} = 5921.34 - 114.4 \cdot C$.

Now, the $CO_2$ concentration may be computed as:

$$PPM_{CO2}(df, C) = -17.4 \cdot (df - (5921.34 - 114.4 \cdot C))$$

Applying this formula to the above-listed measurement results gives the following table of corrections:

| RH [%] | 0 ppm | 500 ppm | 1000 ppm |
|---|---|---|---|
| 0 | 0 | 512 | 1001 |
| 30 | −17 | 484 | 986 |
| 50 | −16 | 474 | 970 |
| 75 | −7 | 458 | 961 |
| 95 | 0 | 458 | 941 |

As seen, the greatest error of −59 ppm occurs in the measurement of the maximum concentration at the maximum ambient humidity. The accuracy of measurements is improved more than by a factor of ten with respect to the prior art.

I claim:

1. A method of measuring the concentration of nonpolar gases by means of a polymer film-coated piezoelectric crystal sensor, comprising:

inferring the amount of the nonpolar gas adsorbed/absorbed in the polymer film (2) from changes in the resonant frequency of the piezoelectric crystal due to changes in the weight of the polymer film (2);

measuring the capacitance of the polymer film (2); and applying a correction to the inferred partial pressure result obtained from the weight measurement, on the basis of the capacitance measurement.

2. A sensor for measuring the concentration of nonpolar gases, said sensor comprising:

a piezoelectric crystal;

a first pair of electrodes formed on opposite surfaces of the crystal for generating oscillations in the crystal;

a polymer film formed on one surface of said crystal; and a second pair of electrodes formed on opposite surfaces of the polymer film wherein the outer electrode is permeable to the gas to be measured.

3. The method according to claim 1, wherein, said correction is a humidity correction function obtained by:

determining the effect of changes in partial pressure of said nonpolar gas on the mass of the polymer film under controlled conditions; and determining the relationship between the capacitance of the polymer film and the mass of the polymer film over the entire ambient relative humidity range at a zero concentration of said nonpolar gas.

4. The method according to claim 3, wherein obtaining said humidity correction function further comprises:

determining the disturbing effect of relative humidity on the adsorption/absorption of the nonpolar gas by the sensor.

5. The method according to claim 1, wherein said nonpolar gas is carbon dioxide.

6. The method according to claim 3, wherein said method is suitable for measuring low concentrations of said nonpolar gas.

7. The method according to claim 4, wherein said method is suitable for measuring high concentrations of said nonpolar gas.

8. The sensor according to claim 2, wherein said piezoelectric crystal is a quartz crystal.

* * * * *